(12) United States Patent
Shanks et al.

(10) Patent No.: US 8,097,029 B2
(45) Date of Patent: *Jan. 17, 2012

(54) STAND-ALONE SCANNING LASER DEVICE

(75) Inventors: Steven C. Shanks, McKinney, TX (US); Kevin B. Tucek, McKinney, TX (US)

(73) Assignee: Erchonia Corporation, McKinney, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/044,885

(22) Filed: Mar. 10, 2011

(65) Prior Publication Data

US 2011/0218598 A1   Sep. 8, 2011

Related U.S. Application Data

(60) Division of application No. 10/976,581, filed on Oct. 29, 2004, now Pat. No. 7,922,751, which is a continuation-in-part of application No. 10/772,738, filed on Feb. 4, 2004, now Pat. No. 7,118,588.

(51) Int. Cl.
*A61N 5/06* (2006.01)
(52) U.S. Cl. .......... 607/89; 606/9; 606/10; 607/88
(58) Field of Classification Search .......... None
See application file for complete search history.

(56) References Cited

U.S. PATENT DOCUMENTS

| | | | | |
|---|---|---|---|---|
| 3,774,162 A * | 11/1973 | Flaherty et al. | | 382/141 |
| 4,965,672 A * | 10/1990 | Duke et al. | | 358/3.02 |
| 5,268,554 A * | 12/1993 | Ream | | 219/121.8 |
| 6,013,096 A * | 1/2000 | Tucek | | 607/89 |
| 6,168,590 B1 * | 1/2001 | Neev | | 606/9 |
| 2001/0053907 A1 * | 12/2001 | Ota | | 606/10 |
| 2002/0104834 A1 * | 8/2002 | Mangiarino et al. | | 219/121.78 |
| 2002/0123781 A1 * | 9/2002 | Shanks et al. | | 607/89 |
| 2003/0189711 A1 * | 10/2003 | Orr et al. | | 356/484 |
| 2003/0218720 A1 * | 11/2003 | Morita et al. | | 351/222 |
| 2004/0106856 A1 * | 6/2004 | Kimura | | 600/310 |

* cited by examiner

*Primary Examiner* — Henry M Johnson, III
*Assistant Examiner* — Lynsey Crandall
(74) *Attorney, Agent, or Firm* — Etherton Law Group, LLC; Benjamin D. Tietgen; Sandra L. Etherton

(57) ABSTRACT

A stand-alone laser device that provides low level laser therapy using one or more laser sources. The laser sources are attached to one or more arms which can be positioned to cause the laser light to impinge on a desired area of a patient's body. A scanning apparatus is attached to the arms which comprise structures that cooperate to cause an optical element to be able to simultaneously rotate about a central axis and move in a linear motion along that axis to achieve any desired scan pattern. Laser light of different pulse widths, different beam shapes and different scan patterns can be applied externally to a patient's body. In the preferred embodiment, red light having a wavelength of about 635 nm is used to stimulate hair growth on a patient's scalp.

6 Claims, 12 Drawing Sheets

STAND-ALONE SCANNING LASER DEVICE

CROSS-REFERENCE TO RELATED APPLICATIONS

This application is a divisional of co-pending U.S. application Ser. No. 10/976,581 filed Oct. 29, 2004, which claims the benefit of U.S. application Ser. No. 10/772,738 filed Feb. 4, 2004.

FIELD OF INVENTION

This invention relates generally to medical and chiropractic devices that employ lasers. More particularly, this invention relates to a stand-alone laser light device that scans a desired area of a patient's body.

BACKGROUND

Low energy laser therapy (LLLT) is used in the treatment of a broad range of conditions. LLLT improves wound healing, reduces edema, and relieves pain of various etiologies, including the treatment and repair of injured muscles and tendons. LLLT is also used during liposuction procedures to facilitate removal of fat by causing intracellular fat to be released into the interstice and post-operatively to reduce inflammation and pain.

LLLT utilizes low level laser energy, that is, the treatment has a dose rate that causes no immediate detectable temperature rise of the treated tissue and no macroscopically visible changes in tissue structure. Consequently, the treated and surrounding tissue is not heated and is not damaged. There are a number of variables in laser therapy including the wavelength of the laser beam, the area impinged by the laser beam, laser energy, pulse width, treatment duration and tissue characteristics. The success of each therapy depends on the relationship and combination of these variables. For example, liposuction may be facilitated with one regimen utilizing a given wavelength and treatment duration, whereas pain may be treated with a regimen utilizing a different wavelength and treatment duration, and inflammation a third regimen.

Laser therapy has also been used as a depilatory to stop hair growth or to eliminate unwanted hair. These devices use relatively high-level laser energy, however, to thermally destroy offending hair follicles. U.S. Pat. No. 5,630,811 issued to Miller describes the evolution of lasers used to remove unwanted hair.

In contrast to the previously-accepted belief that lasers could be used only for hair removal because of the destructive result of the high-level laser energy, LLLT has been recognized recently as a method for hair restoration. One device designed to exploit the biostimulation effects of low level laser therapy to promote hair restoration is described in International Published Patent Application number WO02098509 assigned to Inca Asset Management S.A. of Geneva, Switzerland. This patent application describes a canopy or helmet, similar to the helmets used as hair dyers in hair dressing salons. The device is supported on a stand and positioned over the head of a patient. A helmet-like arrangement is placed inside the canopy so that it can rotate back and forth through about a quarter of a turn.

The invention requires alternate periods of laser stimulation and rest. This is achieved by forming several band shaped formations of laser diodes arranged in two lines on the inside of the helmet. As the helmet is oscillated the illumination from the laser diodes is swept across the scalp of the patient. The two lines are offset so that the scalp is fully illuminated as the helmet is rotated. A control panel on the front of the canopy is used to control the rotation of the helmet and the activation of the laser diodes. An alternate embodiment is described in which a large number of diodes are located on the inside of the helmet so that the entire scalp is illuminated without the need for a rotating canopy. The activation of the laser diodes is controlled to achieve the alternating periods of stimulation and rest required by the invention. A major drawback of this invention is the mechanical requirements to achieve a rotating helmet. Another drawback is the cost of using a large number of laser diodes.

Other methods of hair restoration are known, including hair follicle stimulation by light-emitting diode (LED), massage, and application of hormone-stimulating medicaments. For example, U.S. Pat. No. 6,666,878 issued to Carlgren discloses a helmet having rows of LEDs which create a band of light that moves repeatedly over the area of scalp to be treated. In addition to the discomfort of wearing a helmet repeatedly for extended periods, this device suffers the disadvantage of requiring many LED's to treat the scalp and limiting treatment areas to specific geometries, which can result in uneven hair growth.

Another device, described in U.S. Pat. No. 6,497,719 issued to Pearl et al., uses a laser in combination with a comb. The furrows create an unobstructed path for the laser beam to reach the scalp of the user. However, because each treatment is relatively long and many treatments are required, it is difficult to use a hand-held laser. The user's arm gets tired holding the laser for the required amount of time. This limits the precision and duration of the treatment.

Another hand-held laser is described in the inventor's U.S. Pat. No. 6,013,096. This patent describes a hand-held housing that houses a red semiconductor laser and optics to deliver the beam from the laser to the skin of a patient. A simple timing circuit is provided for controlling the length of time a laser beam is emitted from the housing. An optical arrangement causes the emitted light to form a line on the patient's skin, the shape of the light as it impinges the patient's skin.

Reference may also be had to U.S. Pat. No. 6,746,473 which describes a device that delivers two or more laser beams with different characteristics to treat a patient for multiple types of problems during a single treatment. The patent application describes a hand-held housing that houses a plurality of laser energy sources and optics to direct laser beams from the sources to a patient. Control electronics are provided to vary such parameters as the pulse repetition rate. Optics are also provided to select the beam shape of the laser output, which in turn determines the beam spot.

Both of these devices rely on a static optical arrangement to produce a beam spot. Neither of the devices provides a means for varying the shape or size of the beam spot on demand, nor for automatically varying the resultant intensity. It has become clear in LLLT that there is benefit in being able to customize the delivery of the laser light treatment by changing the shape and energy distribution of the delivered beam spot. It has recently been discovered that overlapping areas of treatment can increase the effects of the therapy. Furthermore, both of these devices are hand-held, requiring a therapist to personally apply the laser therapy. This has the disadvantage of requiring the therapist to continuously attend the patient, as well as limiting the precision and duration of the treatment. It would be desirable to provide a device that can provide accurate and precise treatment to the patient without continuous human intervention.

Therefore, an object of this invention is to provide a laser therapy device that enables shaping of the delivered laser beam to suit multiple types of treatments and treatment patterns, including overlapping scan patterns. It is another object to provide a device that does not have to be held by the user during treatment. Another object is to provide a hair restoration device that does not require the use of a helmet and that provides accurate and precise treatment to the patient without continuous human intervention.

SUMMARY OF THE INVENTION

The present invention is a stand-alone laser device that provides low level laser therapy using one or more laser sources. The laser sources are attached to one or more arms which can be positioned to cause the laser light to impinge on a desired area of a patient's body. A scanning apparatus is attached to the arms which comprise structures that cooperate to cause an optical element to be able to simultaneously rotate about a central axis and move in a linear motion along that axis to achieve any desired scan pattern. Laser light of different pulse widths, different beam shapes and different scan patterns can be applied externally to a patient's body. In the preferred embodiment, red light having a wavelength of about 635 nm is used to stimulate hair growth on a patient's scalp.

BRIEF DESCRIPTION OF THE DRAWINGS

FIG. 6a shows the pushrod in a retracted position; FIG. 6b shows the position in an extended position.

DETAILED DESCRIPTION OF THE INVENTION

Figure 1:
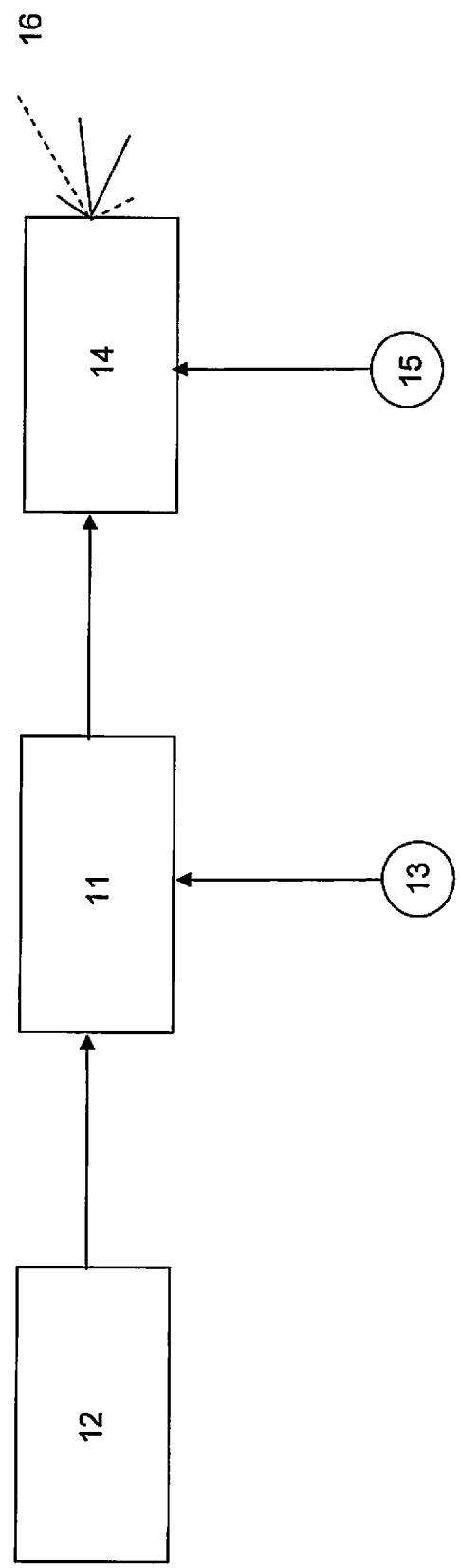
FIG. 1 is a schematic illustration of a preferred embodiment of the present invention.
Figure 2:
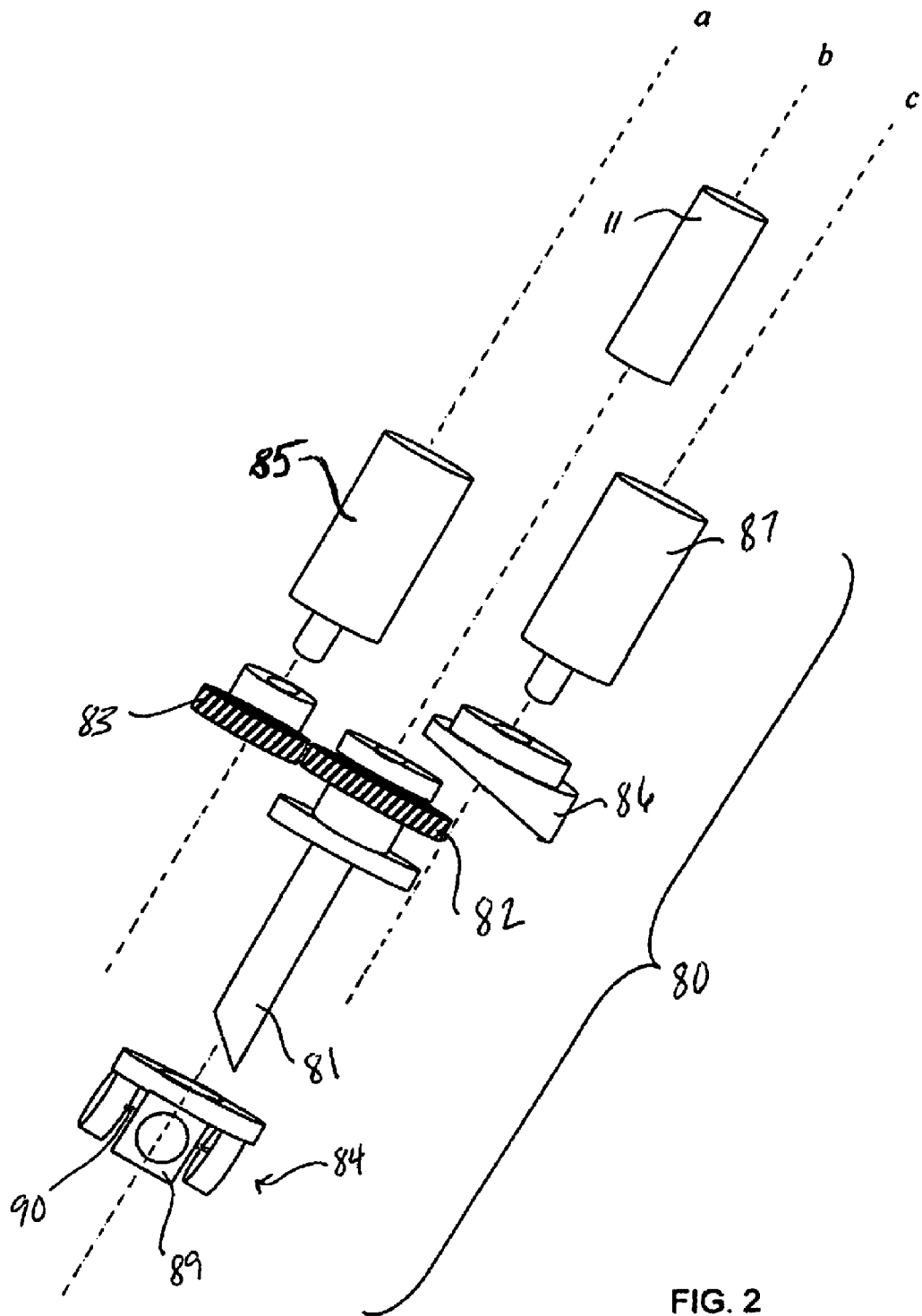
FIG. 2 is perspective view of a scanning head of the preferred embodiment, exploded along axes a, b, and c.
Figure 3:
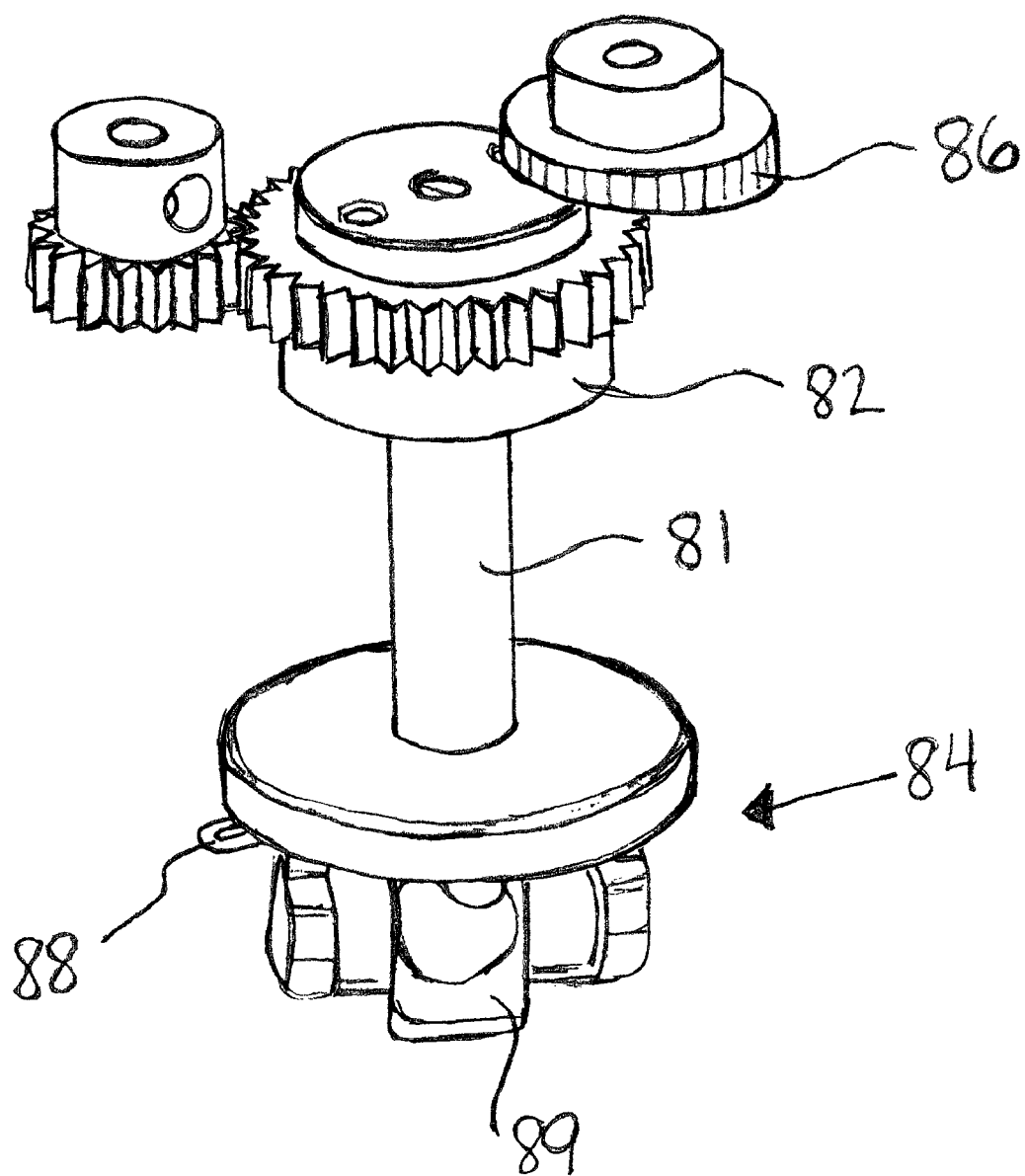
FIG. 3 is a perspective view of the top of the main drive gear.
Figure 4:
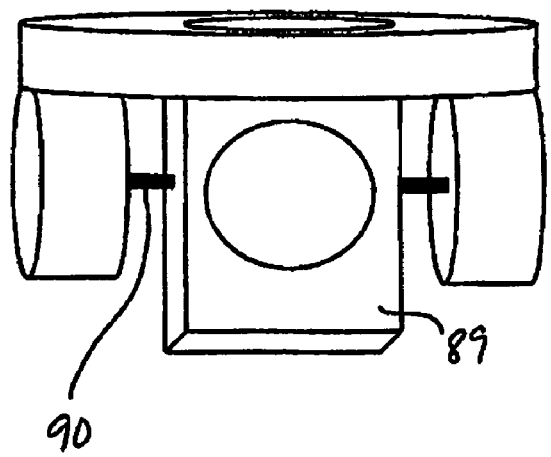
FIG. 4 is a perspective view of the front of the rocker carriage of the preferred embodiment.
Figure 5:
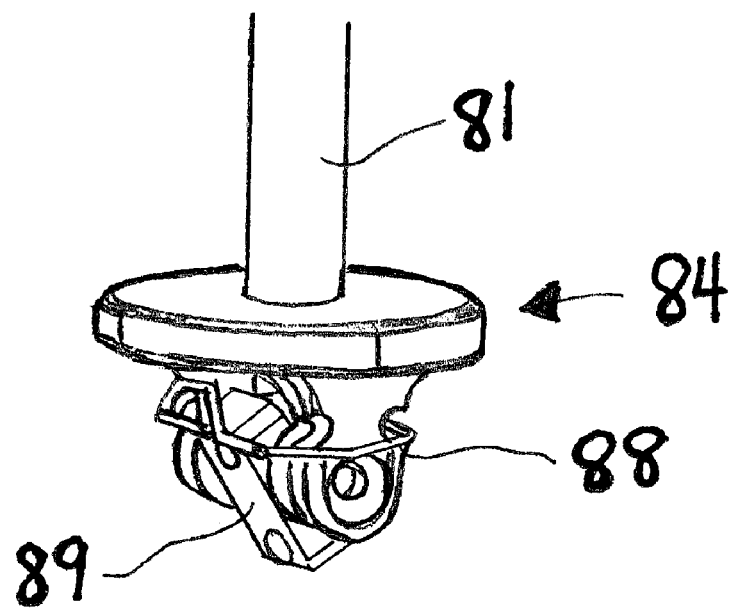
FIG. 5 is a perspective view of the rear of the rocker carriage of the preferred embodiment.

FIG. 1 illustrates a schematic of a laser device that includes a power source 12, at least one laser energy source 11, a laser control 13, a scanning head 14, and a scanner control 15. In the preferred embodiment, the laser control 13 and scanner control 15 are incorporated into a control means 17. The power source preferably provides direct current, such as that provided by a battery, but may instead provide alternating current such as that provided by conventional building outlet power (120V) that is then converted to direct current. The power supply 12 may be housed with the scanning head 14 or may be deployed separately with an electrical cable joining it thereto. Laser control 13 is connected to the laser energy source 11 and acts as on/off switch to control the period of time the laser light is generated and may also have other functions, such as controlling the pulse repetition rate. Other functions of the laser control 13, scanner control 15, and control means 17 are mentioned below.

A scanning mechanism directs the laser beam emitted from the laser source 11 to the patient into any position in front of the scanning head, as depicted by the lines 16. Various means are used to deflect the laser beam in the x, y and z axes by combining a linear movement along a given axis with a circular movement in a plane defined by the other two axes. For example, the movements are a vertical movement along the z axis with a circular movement in the x-y horizontal plane or a horizontal movement in the x axis with a circular movement in the y-z vertical plane. In the preferred embodiment, the laser beam emitted from the laser source 11 is directed to the scanning head 14 which deflects the laser beam into any position within a hemisphere in front of the scanning head. With electronic or computerized control, the scanning head is able to automatically move very quickly, causing the laser beam to appear to create any static shape on the patient's skin. The static shape, however, is actually the result of the scanning light moving from location to location at a speed that makes the motion nearly imperceptible to the human eye. In this way any desired shape of light can be achieved, regardless of the actual cross-sectional shape of the laser beam. Furthermore, the shape can be moved across a desired surface. If the laser is directed to scan across one area more than another, the intensity of the laser therapy is greater in the area of high scan. Similarly, if a laser is directed to scan across an area scanned by another laser, the intensity of the laser therapy is greater in the area of overlapping scans. The size of the spot can also be controlled directly by the scanning head. Because the scanning head is able to automatically move very quickly, the laser beam may be directed to cover an area greater than that of the beam size. The effect of rapid oscillation of the prism and rapid rotation of the scanning head is that a relatively narrow beam can be directed by the scanning head to a whole region substantially simultaneously. The scanning head can produce a curtain of light in a hemisphere below the scanning head or any part of the hemisphere, so virtually any spot size or pattern can be produced on the patient.

FIGS. 2-6 illustrate the preferred embodiment of the scanning apparatus. The structures of this scanning apparatus cooperate to cause an optical element to be able to simultaneously rotate about a central axis and move in a linear motion along that axis. The combination of the rotation and linear motion enables an incident laser beam to be directed to any position in front of the scanning head and therefore to achieve any desired scan pattern.

Figure 6A:
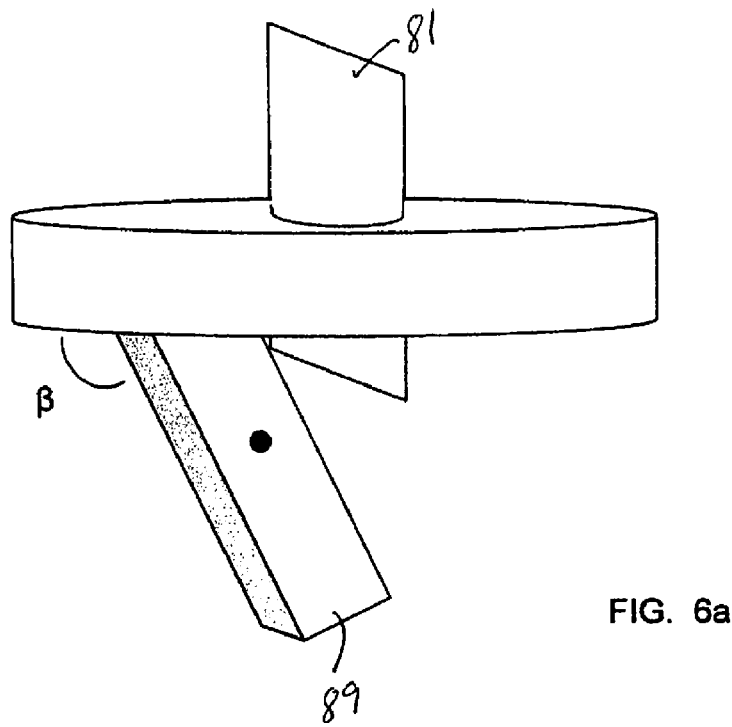
FIGS. 6a and 6b illustrate the effect of moving the pushrod.
Figure 6B:
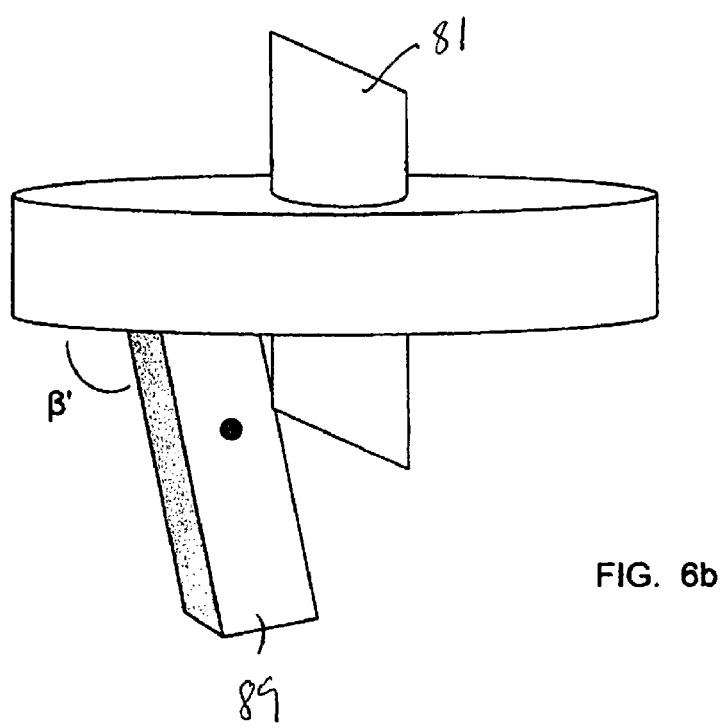

The scanning head 80 comprises a hollow pushrod 81 which extends through central aperture in a main drive gear 82, and further through a central aperture in a rocker carriage 84, all aligned along a central axis b. The leading edge of the pushrod 81 is tapered and touches an optical element 89 which is attached to the rocker carriage 84 on a transverse axle 90. A spring clip 88 biases the optical element 89 against the leading edge of the pushrod 81 such that, as the push rod 81 moves up and down along the central axis a, the optical element 89 slides along the pushrod's leading edge, causing the optical element to rotate about the transverse axle 90. FIG. 6a shows the pushrod in a retracted position, forcing the optical element to angle β. FIG. 6b shows the pushrod in a retracted position, forcing the optical element to angle β'. This causes laser light impinging on the optical element 89 to be reflected (or deflected) parallel to the central axis. The pushrod 81 moves up and down along the central axis b as the result of a beveled cam 86 that abuts the top surface of the pushrod 81. The beveled cam is driven by a cam drive motor 87. As the beveled cam 86 rotates, the pushrod 81 moves up and down along the central axis. Although the optical element 89 is shown as a mirror in this embodiment, it will be appreciated that a prism could also be used.

The rocker carriage 84 is attached to the main drive gear 82 which is mated with a minor drive gear 83. The minor drive gear is driven by a main drive motor 85. The rocker carriage 84 rotates around the central axis b as the main drive gear 82 is turned. Thus, the laser beam from laser energy source 11 passes through the hollow pushrod 81 and strikes an optical element 89 which deflects the laser beam into a desired location.

The position of the optical element in the scanning head is controlled by micromanipulators according to signals received from the scanner control 15, which is preferably incorporated into control means 17. Any suitable mechanism may be employed, but in the preferred embodiment, the main drive motor 85 and cam drive motor 87 are driven electronically according to signals received from the scanner control 15, which is preferably incorporated into control means 17.

Preferably, the control means 17 is further comprised of various discrete circuits, as is known in the art. In a further form, the control electronics is a microprocessor programmed to operate in various modes. The invention is not limited to any particular programmed operation mode, but by way of example the following modes of operation are available.

1. The scanning head is programmed to move through a series of fixed regions and dwell for a pre-set period at each region. The regions may be input by a user to align with particular positions on the scalp that require stimulation.
2. The wavelength is periodically changed by changing the operating laser diode during a repetitive scan. This allows stimulation of the scalp at multiple wavelengths.
3. The focal position of the beam shaping optics is changed to generate smaller or larger spot sizes on the scalp.
4. The laser power is varied.

It will be appreciated that these four modes of operation are indicative and not limiting. Numerous variations and combinations are envisaged by the inventors as being achievable.

While the preferred embodiment utilizes the scanning head 80, other mechanisms for causing laser scan may be used, such as raster scanners like galvanometers, rotating mirrors, speaker scanners; also diffraction grating rotators, light diffusers and the electronics necessary to generate and control image patterns.

Figure 7:
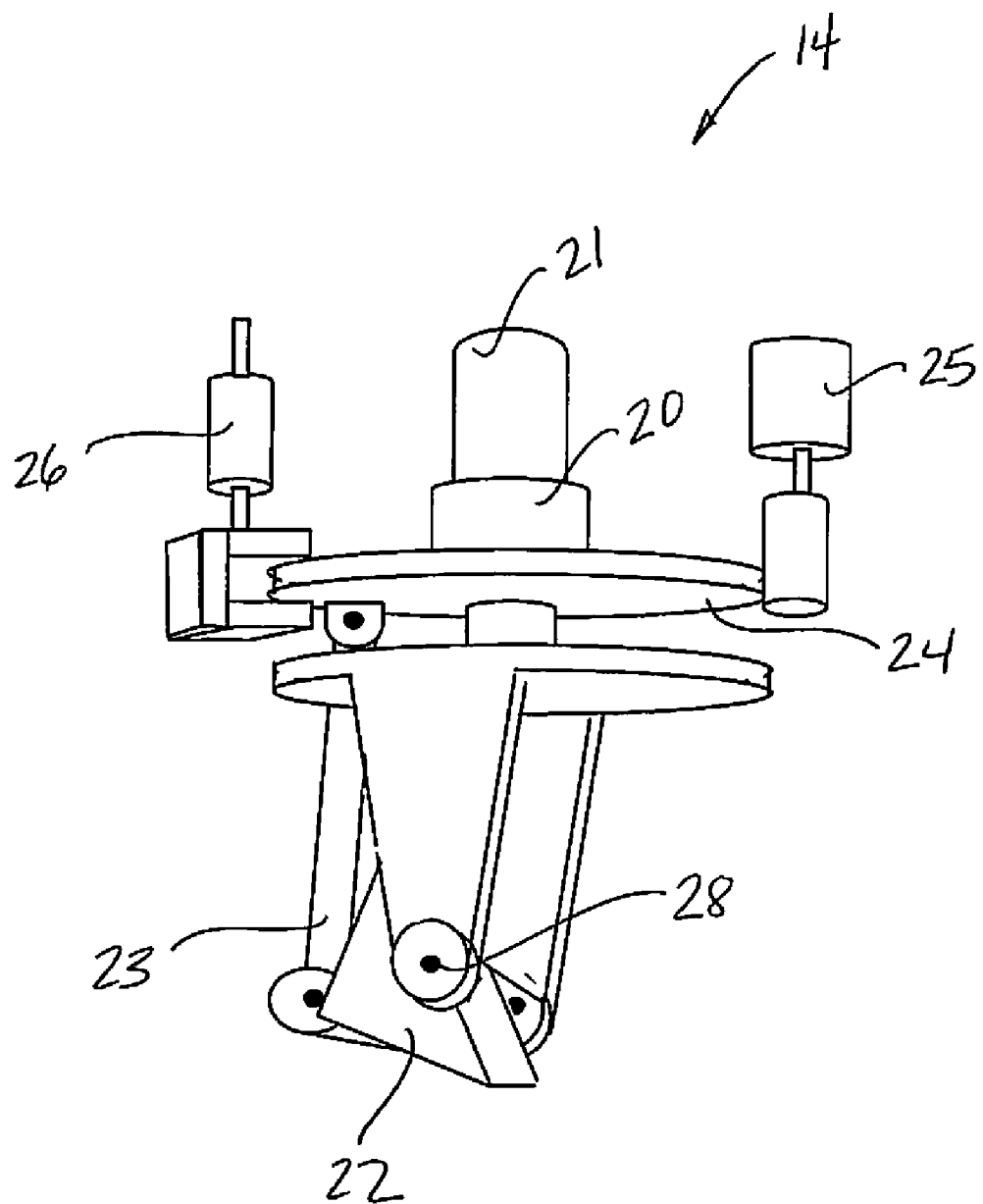
FIG. 7 is a perspective view of an alternate scanning head.

An alternate structure for the scanning head 14 is shown in FIG. 7. The scanning head comprises a hollow spindle 20 mounted on a hollow shaft 21. The laser beam passes through the hollow shaft 21 and strikes an optical element 22 which deflects the laser beam into a desired location. Although the optical element 22 is shown as a prism in this embodiment, it will be appreciated that a mirror could also be used. The optical element 22 is mounted on a transverse axle 28 so that it can rotate through at least 180 degrees. In some applications a lesser degree of travel may be sufficient. The position of the optical element 22 is controlled by a hinged drive arm 23 connected to the optical element at one end and a cam 24 at the other end. The cam 24 is able to travel along the spindle 20 thus causing rotation of the optical element 22. Furthermore, the spindle 20 is able to rotate on the shaft 21. The combination of the rotation of the spindle 20 and movement of the cam 24 positions the optical element so as to direct the laser beam into any position within a hemisphere in front of the scanning head.

The position of the optical element in the scanning head is controlled by micromanipulators according to signals received from the scanner control 15, which is preferably incorporated into control means 17. Any suitable mechanism may be employed, but in the alternate embodiment a motor 25 rotates the cam 24 and a solenoid 26 extends or retracts the cam longitudinally. The combination of rotation and extension of the cam controls the position of the prism or mirror. It will be appreciated that both these functions could be provided by a single micromanipulator acting on the cam 24.

The scanner control 15 is programmed to move the scanning head 14 in a required manner to achieve any desired shape of a treatment zone on the skin of a patient. A sample selection of available scan patterns is shown in FIG. 8a-h. It will be appreciated that the range of available shapes are not limited to those shown in FIG. 8.

Figure 8C:
FIGS. 8a-g shows examples of beam shapes achievable with the present invention.
Figure 8F:
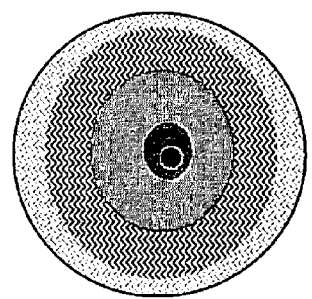
Figure 8B:
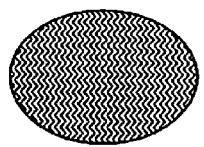
Figure 8E:
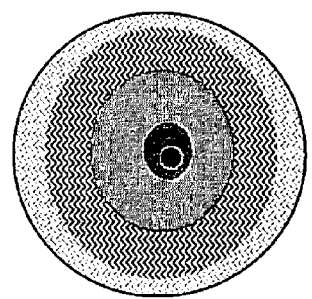
Figure 8A:
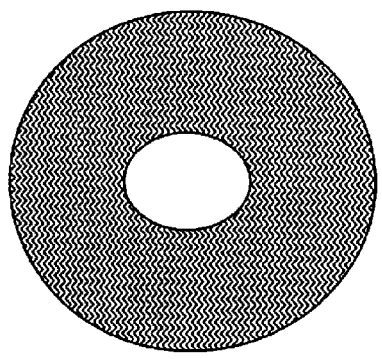
Figure 8D:
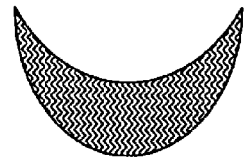
Figure 8G:
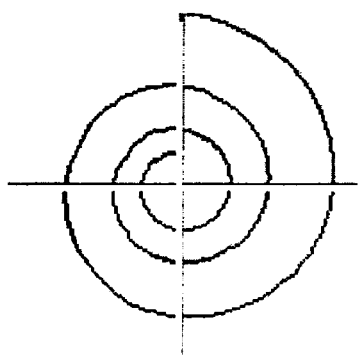
Figure 8H:
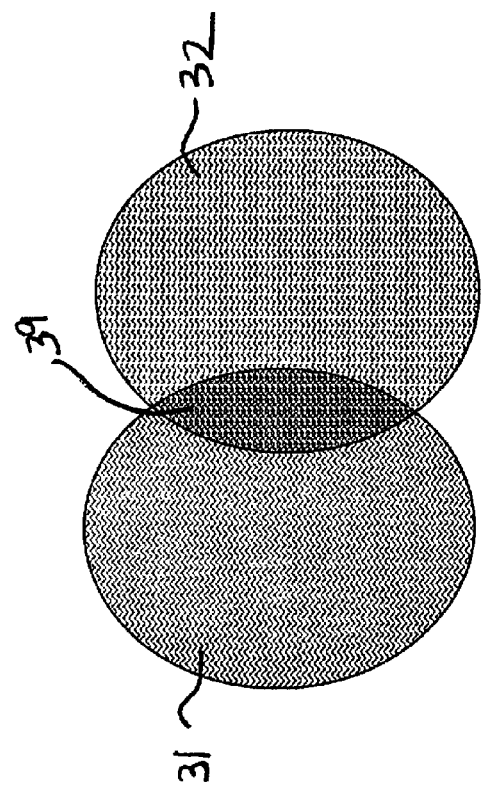
FIG. 8h illustrates overlapping scan patterns.

Furthermore, the scanner control 15 can be programmed to direct the laser output into some regions more than others so that one region may have greater treatment than another region. For example, a donut shaped beam may be produced with less energy delivered to the edges of the donut (an example is shown in FIG. 8a). In this manner the precise energy distribution can be obtained for any given treatment regime. If more than one laser is used, the scanner control 15 can also be programmed to scan across an area scanned by another laser, which causes the energy applied to the surface to be greater in the area of overlapping scans. FIG. 8h shows the overlapping area 39 of a first scan 31 from a first laser source and another scan 32 from a second laser source.

Figure 9:
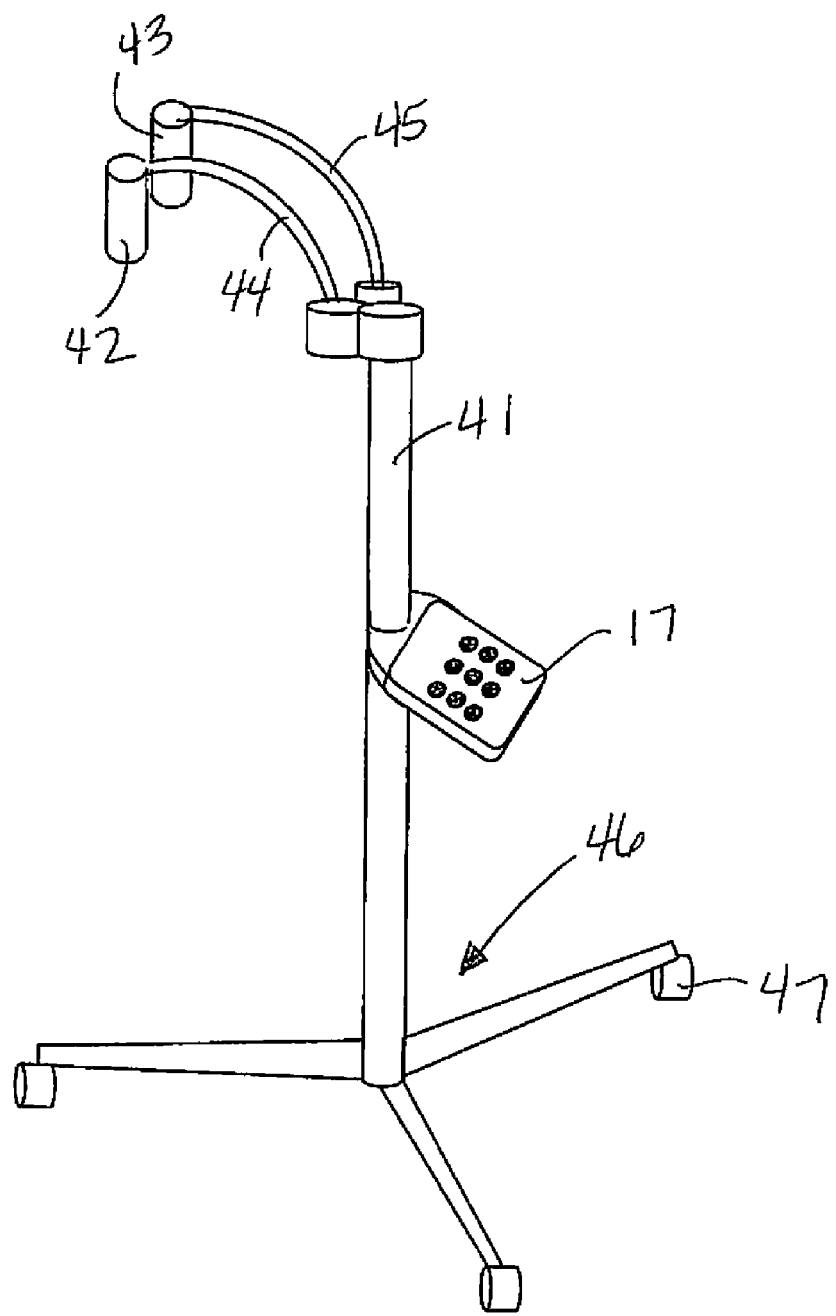
FIG. 9 illustrates a portable, floor-supported version of the preferred embodiment of the present invention.
Figure 10:
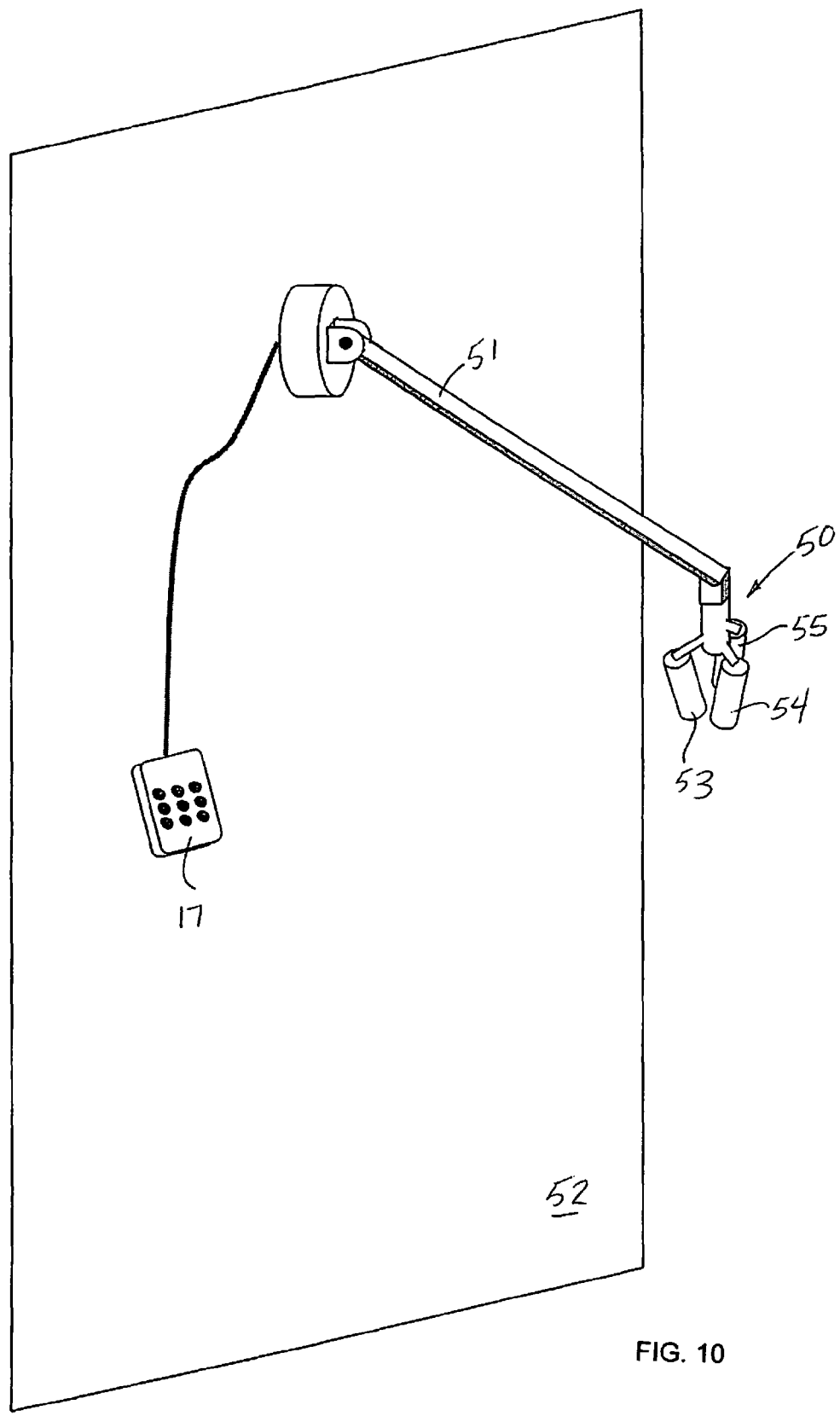
FIG. 10 illustrates a wall-mounted version of the preferred embodiment of the present invention.
Figure 11:
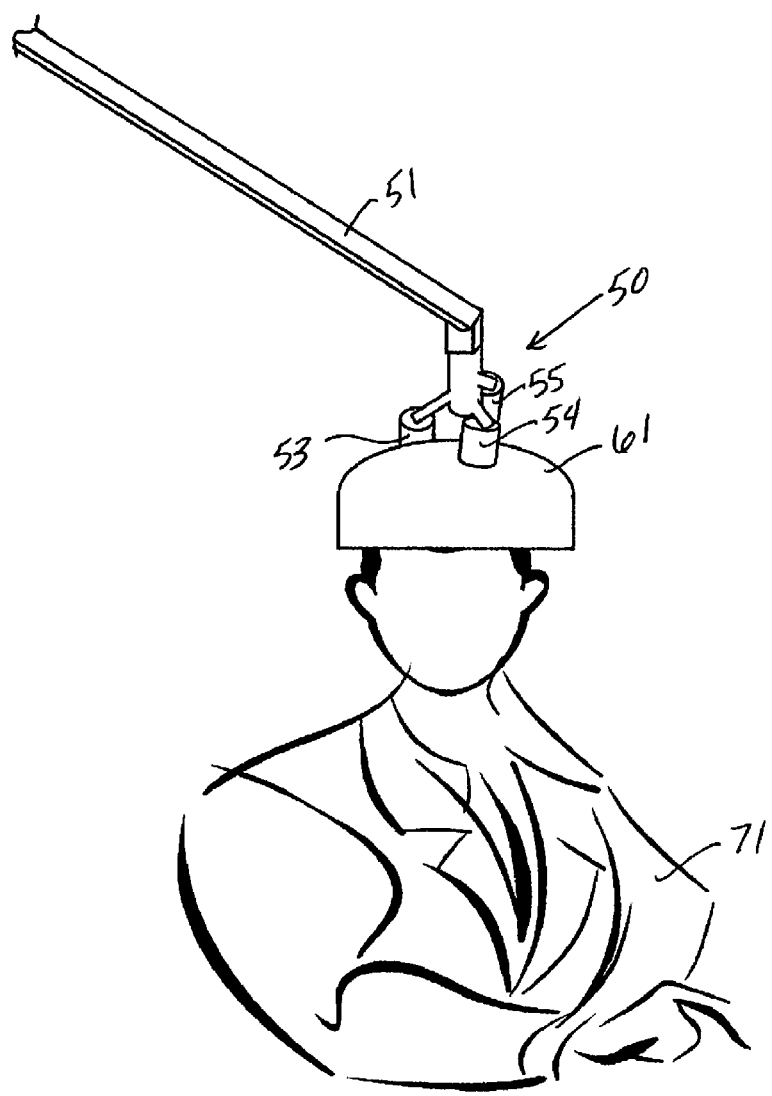
FIG. 11 illustrates a version of the present invention employing a shield.
Figure 12:
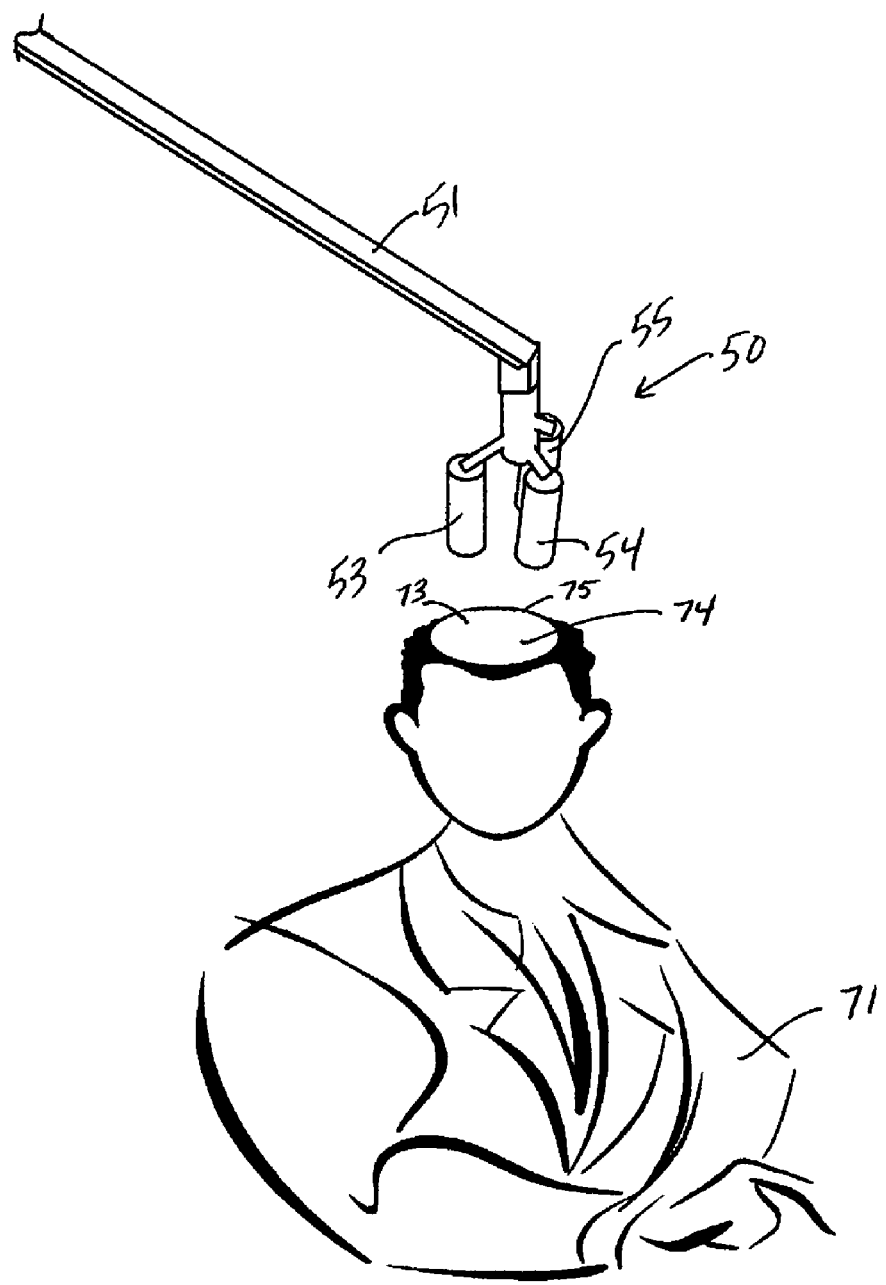
FIG. 12 illustrates the application of low-level laser radiation using the wall-mounted embodiment of the present invention.

In order to direct the laser light to the desired area on a patient, the laser light is emitted from a housing. As shown in FIGS. 9-12 the preferred housing is an elongated hollow tube defining an interior cavity. FIG. 9 shows housings 42 and 43 from which laser light emits. Similarly, FIGS. 10-12 show housings 53, 54, and 55 from which laser light emits. In the preferred embodiment the laser energy source 11 is mounted in the housing's interior cavity, although the laser energy source could be remotely located and the laser light conducted by fiber optics to the housing. The housing may take on any shape that enables the laser light to be directed as needed such as tubular, T-shaped, substantially spherical, or rectangular. As mentioned above, the housing may contain the power supply (for example a battery) or the power supply may be remote with power supplied by an electrical cable. A scanning head may be contained wholly within each housing or attached separately to the end of each housing.

The housing is attached to an arm which is supported by a structure such as the wall or a portable stand that rests on the floor or table. This stand-alone arrangement enables a patient to be scanned by the laser beam without movement of the housing. FIG. 9 shows the portable, floor-mounted version of the present invention. Two-housings 42 and 43 are attached to arm 41 with connectors 44 and 45, respectively. The connectors may be rigid or, preferably, flexible, so that the housings can be moved to any desired position. The arm 41 may be articulated for additional control over the position of the lasers. The arm 41 is attached to a base 46 having wheels 47 such that the device can be moved to any desired position and then stay substantially stationary while treatment is occurring. This is particularly convenient for patients lying on a table or sitting in wheelchair. Control means 17 is in electrical connection with the housings and is shown in FIG. 9 mounted on the arm 41. The control, however, can be mounted elsewhere or can operate as a remote control using radio frequencies or other methods known in the art.

FIG. 10 shows a three-housing assembly 50 attached to a wall-mounted arm 51. The arm 51 is affixed to the wall 52 in ways known in the art such that it can be moved to any desired position and then stay in substantially stationary while treatment is occurring. The arm may be articulated for additional control over the position of the lasers. Control means 17 is in electrical connection with the housings and is shown in FIG. 10 mounted on the wall. The control, however, can be mounted elsewhere or can operate as a remote control using radio frequencies or other methods known in the art. The assembly 50 is attached to the arm 51 in ways known in the art such that it can be moved to any desired position. Likewise, the housings 53, 54, 55 are attached to the assembly so that each can be moved to a desired position.

A shield may be employed to prevent the laser light from reflecting or deflecting to undesired locations. The shield is attached where appropriate to block the radiation. For example, the shield 61 may be attached to the assembly, to one or more of the housings, or worn by the patient. FIG. 11 illustrates a shield 61 that blocks the laser light that may reflect or deflect off the patient's head. It is shaped like a canopy or helmet and preferably is attached to the assembly 50 such that the housings 53, 54, 55 protrude through the shield 61 to ensure that no laser light escapes the canopy. The shield may take on other shapes, as appropriate, depending on the area to be shielded. For example, the shield may take on a rectangular or hemi-cylindrical shape to shield a patient's upper torso.

FIG. 12 illustrates the application of low-level laser radiation for hair restoration using the wall-mounted embodiment of the present invention. Patient 71 is balding and the laser assembly 50 is positioned above his head. The patient can remain comfortably seated or lying on a table throughout the treatment and no therapist intervention is required to treat the patient.

In the preferred embodiment, each housing 53, 54, 55 is directed by the control means 17 to deliver a desired scan pattern 73, 74, 75 respectively with a desired laser output across the patient's scalp. Due to the nature of the laser light, the patent can be treated through any existing hair, so it is unnecessary to touch the hair or scalp to clear a pathway for the laser light.

Most laser hair treatment modalities have proven to be effective at a single wavelength in the red region of the spectrum, between about 630 nm and about 670 nm. However, it has been shown that LLLT can be effective throughout the visible, near infrared and near ultraviolet regions. Laser diodes are currently available to cover only a limited part of the available spectrum, so other laser energy sources may be used. To obtain maximum benefit it may be desirable to stimulate the scalp at two or more different wavelengths. Persons skilled in the art will be aware that various laser energy sources are known in the art for use in low-level laser therapy. They include Helium-Neon lasers having a 632 nm wavelength and semiconductor diode lasers with a broad range of wavelengths between 600-800 nm. The laser energy source in the preferred embodiment is a semiconductor laser diode that produces light in the red range of the visible spectrum, having a wavelength of about 635 nm. Other suitable wavelengths are used for other particular applications. While many LLLT regimen include ultraviolet or infrared laser light, it is advantageous to utilize at least one laser beam in the visible energy spectrum so that the operator can see the laser light as it impinges the patent's body and the area treated can be easily defined.

The preferred embodiment is described as having a single laser energy source 11 but it will be appreciated that the invention may have two or more laser energy sources. These laser sources may be attached to each other in a laser assembly or individually attached to a support structure, as described in more detail below.

Different therapy regimens require diodes of different wattages. The preferred laser diodes use less than one watt of power each to simultaneously facilitate liposuction, treat post-operative inflammation and post-operative pain, as well as to restore hair. Diodes of various other wattages may also be employed to achieve the desired laser energy for the given regimen. It may be advantageous to provide a power source separate from the housing, and deliver the power to the housing by wire. An advantage of the present invention is that a larger treatment area can be achieved without the need for a higher power laser. Furthermore, by careful choice of scan pattern, the available laser light can be used more efficiently than is achievable with the prior art LLLT devices.

Laser control 13, preferably incorporated into control means 17, controls the duration of each pulse of laser light emitted and the repetition rate. When there are no pulses, a continuous beam of laser light is generated. Repetition rates from 0 to 100,000 Hz or more may be employed to achieve the desired effect on the patient's tissue. The goal for LLLT regimen is to deliver laser energy to the target tissue utilizing a pulse width short enough to sufficiently energize the targeted tissue and avoid thermal damage to adjacent tissue.

While there has been illustrated and described what is at present considered to be a preferred embodiment of the present invention, it will be understood by those skilled in the art that various changes and modifications may be made, and equivalents may be substituted for elements thereof without departing from the true scope of the invention. Therefore, it is intended that this invention not be limited to the particular embodiment disclosed as the best mode contemplated for carrying out the invention, but that the invention will include all embodiments falling within the scope of the appended claims.

We claim:

1. A laser device comprising:
   a) at least one laser energy source for generating a laser beam;
   b) a scanning head connected to a housing that directs the laser beam into any location forward of the scanning head; and
   c) a support structure connected to laser energy source which enables a patient to be scanned by the laser beam without moving the laser energy source;
   wherein the scanning head comprises: a spindle mounted for rotation on a hollow shaft; an optical element mounted on the spindle and rotatable in a plane perpendicular to a plane of rotation of the spindle; a cam slidably mounted on the spindle and rotatable with the spindle; and a hinged arm joining the cam to the optical element such that the sliding motion of the cam on the spindle causes rotation of the optical element relative to the spindle.

2. A therapeutic laser device comprising:
   a) a laser energy source generating a laser beam;
   b) a scanning head for receiving the laser beam and for directing the laser beam into a desired location, the scanning head comprising a spindle mounted for rotation on a hollow shaft, an optical element mounted on the spindle and rotatable in a plane perpendicular to a plane of rotation of the spindle, a cam slidably mounted on the spindle and rotatable with the spindle, and a hinged arm joining the cam to the optical element such that the sliding motion of the cam on the spindle causes rotation of the optical element relative to the spindle; and c) a control circuit for controlling the scanning head to direct the laser beam to form a desired scan pattern.

3. The device according to claim 2 further comprising a housing from which the laser beam emits, the housing having an interior cavity within which the scanning head is mounted.

4. The laser device according to claim 2 wherein the optical element is a mirror.

5. The laser device according to claim 2 wherein the optical element is a prism.

6. The laser device according to claim 2 further comprising a shield positioned such that the laser beam emitted from the housing is blocked from being reflected or deflected to undesirable locations.

* * * * *